United States Patent
Hiroi et al.

(10) Patent No.: US 8,509,516 B2
(45) Date of Patent: Aug. 13, 2013

(54) CIRCUIT PATTERN EXAMINING APPARATUS AND CIRCUIT PATTERN EXAMINING METHOD

(75) Inventors: Takashi Hiroi, Yokohama (JP); Takeyuki Yoshida, Hitachinaka (JP); Naoki Hosoya, Tokyo (JP); Toshifumi Honda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 176 days.

(21) Appl. No.: 13/056,046

(22) PCT Filed: Jul. 13, 2009

(86) PCT No.: PCT/JP2009/063012
§ 371 (c)(1),
(2), (4) Date: Jan. 26, 2011

(87) PCT Pub. No.: WO2010/013612
PCT Pub. Date: Feb. 4, 2010

(65) Prior Publication Data
US 2011/0129141 A1 Jun. 2, 2011

(30) Foreign Application Priority Data
Jul. 30, 2008 (JP) .................. 2008-195606

(51) Int. Cl.
*G06K 9/00* (2006.01)
(52) U.S. Cl.
USPC ............................ 382/145; 382/218; 382/144
(58) Field of Classification Search
USPC .......................................... 382/142, 145, 149
See application file for complete search history.

(56) References Cited

U.S. PATENT DOCUMENTS

| | | | |
|---|---|---|---|
| 5,173,719 A | 12/1992 | Taniguchi et al. | |
| 7,071,468 B2* | 7/2006 | Miyai et al. | 250/310 |
| 7,327,871 B2* | 2/2008 | Ishikawa | 382/145 |
| 7,492,942 B2* | 2/2009 | Ishikawa et al. | 382/145 |
| 7,764,825 B2* | 7/2010 | Oaki | 382/149 |
| 8,121,390 B2* | 2/2012 | Nagano | 382/141 |
| 2004/0218808 A1 | 11/2004 | Prince | |

(Continued)

FOREIGN PATENT DOCUMENTS

| | | |
|---|---|---|
| JP | 3-232250 | 10/1991 |
| JP | 2001-209798 | 8/2001 |

(Continued)

OTHER PUBLICATIONS

Japanese Office Action with English translation issued in Japanese Appliction No. 2008-195606 mailed Dec. 4, 2012.

*Primary Examiner* — Gregory M Desire
(74) *Attorney, Agent, or Firm* — McDermott Will & Emery LLP (57) ABSTRACT

Provided is an examination technique to detect defects with high sensitivity at an outer-most repetitive portion of a memory mat of a semiconductor device and even in a peripheral circuit having no repetitiveness.

A circuit pattern inspection apparatus comprises an image detection unit for acquiring an image of a circuit pattern composed of multiple die having a repetitive pattern, a defect judgment unit which composes, in respect of an acquired detected image, reference images by switching addition objectives depending on regions of repetitive pattern and the other regions and compares a composed reference image with the detected image to detect a defect, and a display unit for displaying the image of the detected defect.

13 Claims, 12 Drawing Sheets

(56) References Cited

U.S. PATENT DOCUMENTS

| | | |
|---|---|---|
| 2005/0117796 A1 | 6/2005 | Matsui et al. |
| 2006/0159330 A1 | 7/2006 | Sakai et al. |
| 2006/0222232 A1* | 10/2006 | Ishikawa ................ 382/141 |
| 2006/0280358 A1* | 12/2006 | Ishikawa ................ 382/149 |
| 2008/0030200 A1* | 2/2008 | Ueyama .................. 324/512 |
| 2008/0166054 A1* | 7/2008 | Tsuchiya et al. ........ 382/194 |
| 2008/0172196 A1* | 7/2008 | Kang et al. ............... 702/81 |
| 2009/0037134 A1* | 2/2009 | Kulkarni et al. ......... 702/127 |
| 2011/0129141 A1* | 6/2011 | Hiroi et al. .............. 382/149 |

FOREIGN PATENT DOCUMENTS

| | | |
|---|---|---|
| JP | 2004-028836 A | 1/2004 |
| JP | 2005-156475 A | 6/2005 |
| JP | 2006-220644 | 8/2006 |
| JP | 2007-514167 A | 5/2007 |

* cited by examiner

RECIPE PREPARATION PROCEDURES

INSPECTION PROCEDURES

CIRCUIT PATTERN EXAMINING APPARATUS AND CIRCUIT PATTERN EXAMINING METHOD

RELATED APPLICATIONS

This application is the U.S. National Phase under 35 U.S.C. §371 of International Application No. PCT/JP2009/063012, filed on Jul. 13, 2009, which in turn claims the benefit of Japanese Application No. 2008-195606, filed on Jul. 30, 2008, the disclosures of which Applications are incorporated by reference herein.

TECHNICAL FIELD

The present invention relates to a technique to inspect a substrate unit having a circuit pattern of, for example, a semiconductor device or liquid crystals by utilizing light or an electron beam.

BACKGROUND ART

An inspection apparatus for a circuit pattern of a semiconductor device or liquid crystals has the function to compare an image obtained under irradiation of light or an electron beam with a reference image represented by a standard image or an adjoining image, extract a pixel affected by a difference to judge it as a defect and output a coordinate thereof.

In a circuit pattern as a target of the inspection apparatus, the pattern density per unit area has been quadrupping every 3 years. This is realized by the pattern shrinkage. The shrinkage causes the difference between a defect and a normal portion becomes very small. Then, by setting a threshold value between a signal value of the defect and that of the normal portion and discriminating the defect from the normal portion, a minute defect can be detected. Especially, in a memory mat of a memory device, one memory cell is one bit of memory, but even if a defect is present in a single memory cell, the total device can operate normally by virtue of a redundancy circuit technique and therefore, the miniaturization is further spurred. On the other hand, in a peripheral circuit other than the memory mat, even a single defect causes the device defective and so the pattern dimension is not so miniaturized as in the case of the memory mat. When reviewing a distribution of locations where pattern defects occurs, it is indicated that the density of defects is high in the memory mat. Especially, at the outer-most of the memory mat, the pattern density changes abruptly and hence, production in photolithography process is very difficult and the defect density is very high.

A technique for inspecting such a periodical pattern portion as in the memory mat and a region having no repetiveness discriminatively from each other has been known (see Patent Literature 1). But a technique capable of detecting defects in both of them at a same time with high accuracies has not yet been known.

In inspecting a semiconductor wafer in which semiconductor devices are formed, there are die to die comparison method and a cell comparison method which inspect only cell region having pattern repetiveness in a die. The cell comparison method uses the repetiveness and cannot be applied to a peripheral circuit without repetiveness.

Citation List
Patent Literature
Patent Literature 1: JP-A-3-232250

SUMMARY OF INVENTION

Technical Problem

The present invention intends to provide an inspection technique which can judge defects with high sensitivity in the outer-most periphery of the memory mat of semiconductor device and even in the peripheral circuit without repetiveness as well.

Solution to Problem

To solve the aforementioned problems, an embodiment of the present invention comprises an image detection unit for acquiring an image of a circuit pattern composed of multiple die each having a repetitive pattern, and a defect judgement unit which composes, in respect of an acquired detected image, reference images by switching addition objectives depending on regions of repetitive pattern and the other regions and compares a composed reference image with the detected image to detect a defect.

Advantageous Effects of Invention

According to the present invention, an inspection technique which can judge defects with high sensitivity in the outer-most periphery of the memory mat of semiconductor device and even in the peripheral circuit without repetiveness as well is realized.

DESCRIPTION OF EMBODIMENTS

Figure 1:
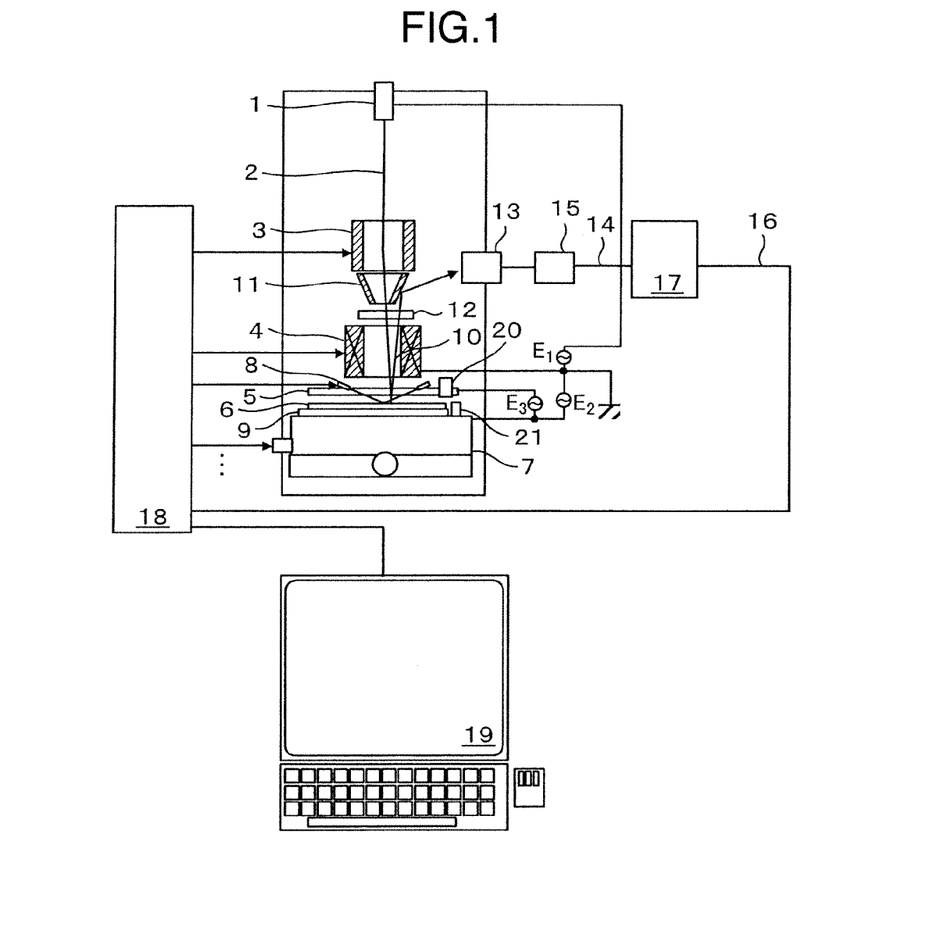
FIG. 1 is a diagram showing the overall configuration of a circuit pattern inspection apparatus.

An embodiment of the present invention will now be described with reference to the drawings. FIG. 1 is a diagram showing the overall configuration of a circuit pattern inspection apparatus, illustrating a principal portion in a cross-sectional form. In the present embodiment, an inspection apparatus will be described. It is a scanning electron microscope adapted to obtain an image by irradiating an electron beam on a sample. The principal portion of the invention is same when light is used in place of the election beam. Therefore, a description will not be given herein of an embodiment of an optical inspection apparatus.

In FIG. 1, electrons 2 come from an electron source 1 irradiate a semiconductor wafer 6. The electrons 2 are focused finely by an objective lens 4 and are deflected by a deflector 3 so as to scan the surface of semiconductor wafer 6. Since the semiconductor wafer 6 that is under irradiation of the electrons 2, are charged up and an image to be obtained will sometimes become white or, conversely, black, according to difference in material characteristics and structure. Therefore, a charge-up control electrode 5 is provided for the purpose of controlling the charge-up.

The semiconductor wafer 6 is mounted on an XY stage 7 through a sample holder 9 and can be moved in X direction and Y direction. The measured position of the XY stage 7 is sent to an overall control unit 18, so that the deflector 3, objective lens 4 and XY stage 7 are controlled in such a manner that the electrons 2 are irradiated on a intended location of the semiconductor wafer 6. The height of semiconductor wafer 6 is measured by a Z sensor 8 and height data is sent to the overall control unit 18, so that the focus of electrons 2 is controlled to be made on the semiconductor wafer 6.

Signals 10 of secondary electrons and reflected electrons generated under irradiation of the electrons 2 may have various kinds of energy and direction and therefore, must be converged so as to be detected by a detector 13. In the present embodiment, a reflection plate 11 and a converging optical system 12 are provided to capture secondary electron as much as possible.

The analog signal detected by the detector 13 is converted by an AD converter 15 into a digital signal 14, and a defect judgement unit 17 extract defect information 16, and the defect information 16 is sent to the overall control unit 18 so as to enable the image to be displayed on a console 19. The console 19 displays the image and complementary information such as coordinates of the defect and besides, and also inform designation by an operator to the overall control unit 18r.

An optical microscope 20 is arranged above the sample holder 9 to capture an optical image of the semiconductor wafer 6 and position matching is carried out prior to inspection. A standard sample piece 21 is mounted on the XY stage 7 for detailed adjustment of electron optical condition, having its height set to be equal to that of the semiconductor wafer 6.

Figure 2:
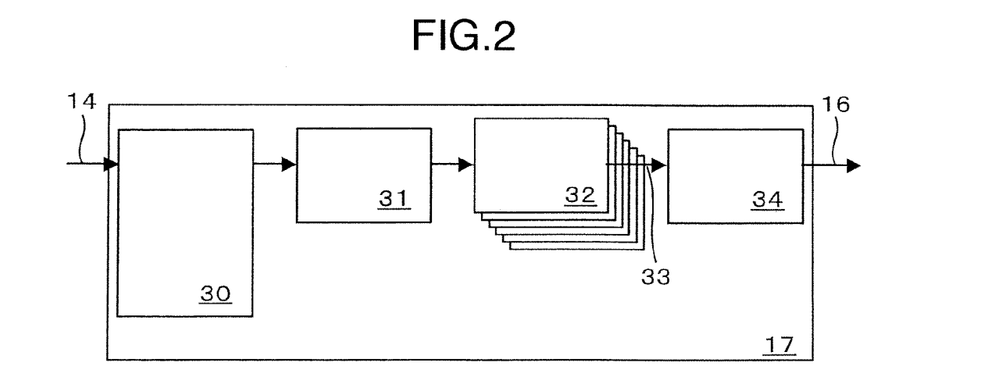
FIG. 2 is a diagram showing the construction of a defect judgement unit.

The defect judgement unit 17 is shown in FIG. 2. The defect judgement unit 17 is a unit for processing the digital signal 14 as a two-dimensional digital image. The unit 17 is composed of an image memory 30 for storing the digital signal 14, an image distributor 31 for distributing digital images stored in the image memory 30 according to the indicated regional information of the image, plural PEs 32 for extracting defects on distributed partial images, and an information unifier 34 for unifying defect information on distributed partial images 33, processed by the plural PEs 32 to provide defect information 16. The PE referred to herein is short for Processor Element. The information unifier 34 totals defect information on distributed partial image 33 from all of the PEs 32 and outputs, as defect information 16, information of a defect so determined through either FR-MA (Full region reference image averaging) method or die comparison.

Figure 3:
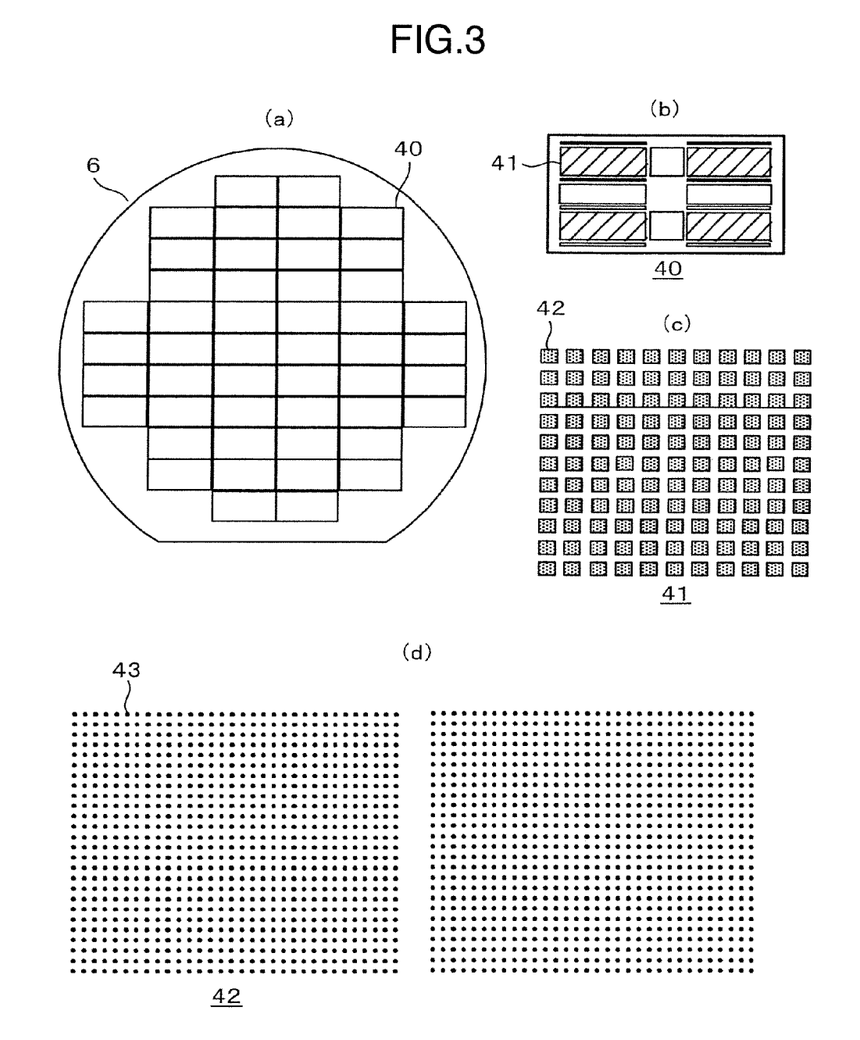
FIG. 3 is a plan view of a semiconductor wafer.

FIG. 3 illustrates the semiconductor wafer in plan view form. An overall diagram is shown in (a), an enlarged diagram of a die is shown in (b), a diagram indicative of arrangement of cells in the die is shown in (c), and an enlarged diagram of the cell is shown in (d). As shown in FIG. 3 (a), the semiconductor wafer 6 is discotic having a diameter of 200 mm to 300 mm and a thickness of about 1 mm and having its surface formed with several hundreds to several thousands of semiconductor device. The semiconductor device is called a die and after being formed with the circuit patterns, is cut, and is packaged. In the case of a general-purpose memory device, a die 40 has four memory mat groups 41 as shown in FIG. 3 (b). A single memory mat group 41 is composed of memory mats 42 amounting up to approximately 100 in vertical direction and 100 in horizontal direction as shown in FIG. 3 (c). A single memory mat 42 is composed of several millions of memory cells 43 having repetiveness in two-dimensional directions as shown in FIG. 3 (d).

Figure 4:
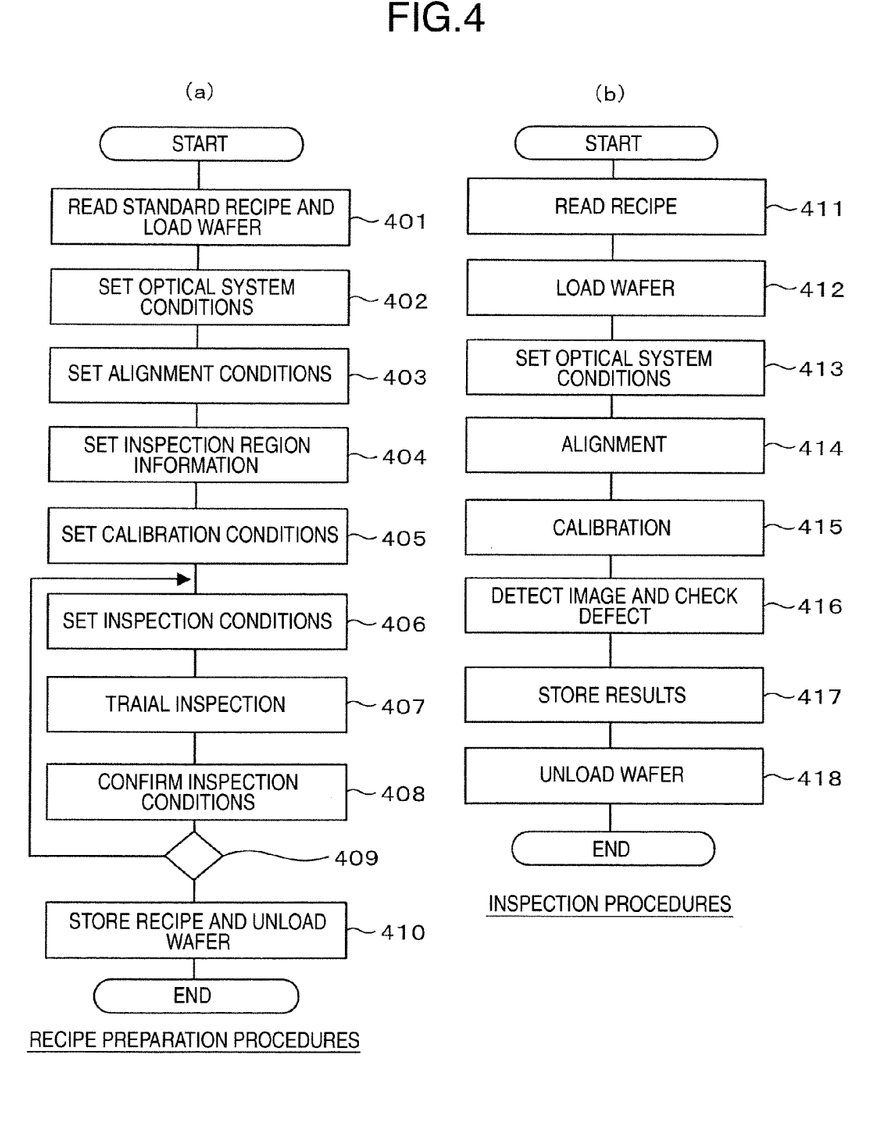
FIG. 4 is a flowchart showing a recipe preparation procedure and an inspection procedure.

FIG. 4 is a flowchart showing recipe preparation procedures and inspection procedures. Since inspection conditions are required to be determined and registered in the apparatus in advance of inspection, a recipe for inspection is prepared and an inspection is carried out in accordance with the prepared recipe.

The operator prepares a recipe by using the console 19 shown in FIG. 1. A standard recipe of standard conditions is preset and hence, the operator gives instructions to the overall control unit 18 to read the standard recipe and subsequently, in order that the contents of the recipe is corrected by actually irradiating electrons on a semiconductor wafer, loads the semiconductor wafer on the apparatus (step 401).

Optical system conditions are subsequently set but instead, mere confirmation of set values of the standard recipe may suffice (step 402). The optical conditions are composed of a parameter for extracting electrons 2 from the electron source 1, a parameter for setting the intensity of the objective lens 4, a control parameter for the deflector 3, and a voltage to be applied to the charge-up control electrode 5. The electrons 2 are irradiated on the standard sample piece 21 to capture its image, the operator modifies the setting values of optical conditions while watching the image to rewrite them to proper values and make the new recipe to be read into the overall control unit 18.

Next, a pattern for alignment of the loaded semiconductor wafer 6 and its coordinates are registered for alignment (step 403). The pattern for alignment is, i.e., at die corner.

Next, information of an inspection region representing an inspection objective is set (step 404). A pattern layout of semiconductor wafer 6 read in advance is displayed on the display of console 19.

In the case of cell comparison inspection, the memory mat 42 is designated as a repeative region for comparison. On the display, the memory mat 42 can be designated by depressing a designation button adapted to surround the memory mat with a rectangular figure so as to designate it as a repeative region. Further, it is necessary to perform a region designation indicating that the comparison inspection of memory mat 42 will proceed from which one of memory mats to which one of memory mats and for example, in the drawing as shown in FIG. 3 (b), one of the memory mat groups 41 is designated.

In the case of die comparison, one arbitrary die 40 is designated as a repeative region standing for a unit of comparison in connection with the drawing of the overall wafer shown in FIG. 3 (a). In case all of the dies are targeted for a comparison inspection, a button called an all die comparison inspection may conveniently be provided. If only a die positioned at a specified location is subjected to fixed-point monitoring, the inspection die is rendered selectable. Preferably, a screen layout may be prepared to permit, for example, directly clicking a die on the screen or designating a region by surrounding it with a rectangular figure.

Next, calibration conditions are set (step 405). In order to prevent unevenness in detection light quantity in respect of individual semiconductor wafers 6, the light quantity is calibrated to permit inspection to be carried out under a constant condition. An arbitrary coordinate point of the semiconductor wafer 6 is designated and an initial gain of the detector 13 is set. Next, conditions for image processing, for example, a pixel dimension and a frequency of frame additions are selected or designated. The set inspection conditions are set to the overall control unit 18 (step 406).

Subsequently, to confirm whether the set inspection conditions are proper or not, a trial inspection is conducted in which electrons are actually irradiated and an image is obtained (step 407). Details of the trial inspection will be described with reference to FIG. 5. On the basis of a result of the trial inspection, the operator makes a decision whether the inspection conditions are proper or not (step 409). In case of not proper, the program returns to the step 406. In case of proper, the inspection conditions are stored as a new recipe to the overall control unit 18 and the semiconductor wafer 6 is unloaded from the apparatus (step 410).

Figure 5:
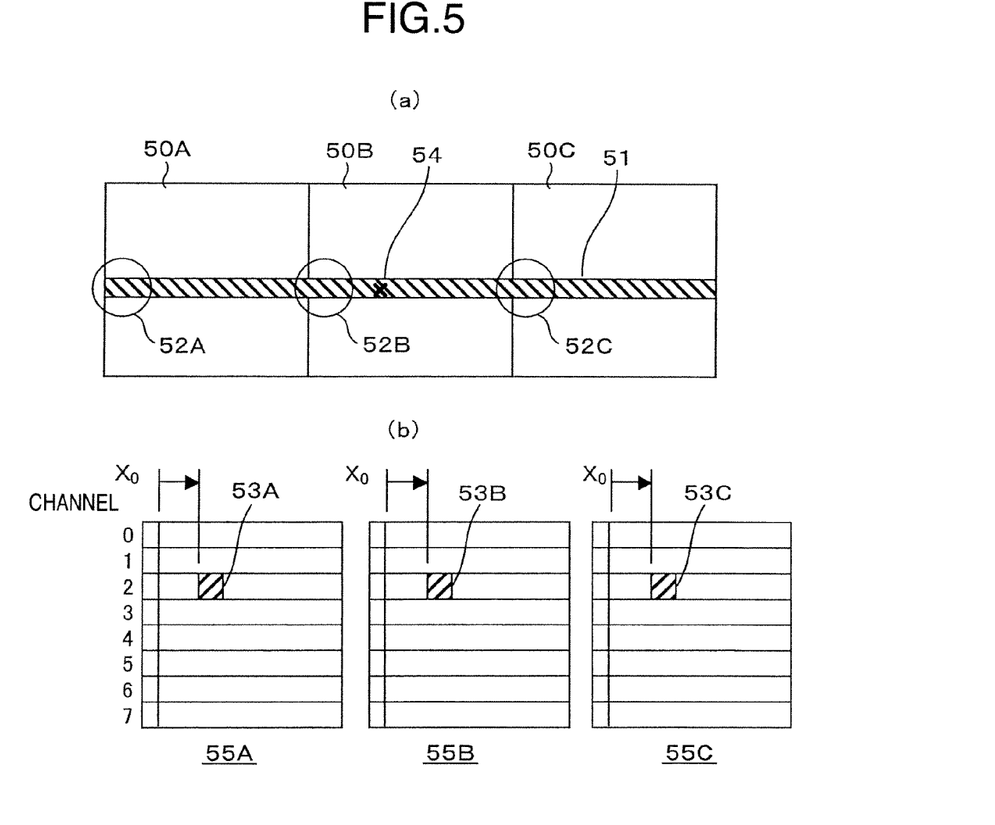
FIG. 5 is a diagram showing diagrammatically the contents of an image processing in a trial inspection.

The contents of image processing in the trial inspection is illustrated diagrammatically in FIG. 5. In FIG. 5 (*a*), a trail inspection coordinate 54 through which a trial inspection is carried out is designated in one die image 50B out of die images 50A, 50B and 50C. As execution of the trial inspection then proceeds, electrons are irradiated on an elongated rectangular stripe area 51 having a length corresponding to an electron travel length through a total of 3 dies of the designated die 50B, one die preceding it and one die succeeding it and a width corresponding to an electron scan width, and a generated signal 10 is detected by means of the detector 13. At that time, on the basis of a height of semiconductor wafer 6 detected by the Z sensor, the excitation current value of the objective lens 4 is controlled and the focal position of electrons is corrected. The analog signal detected by the detector 13 is converted into a digital signal by means of the AD converter 15 and formed to an image.

FIG. 5 (*b*) is a status in which pieces of image data 53A, 53B and 53C of areas 52A, 52B and 52C are stored at locations on a channel 2 in memory regions 55A, 55B and 55C not shown in the defect judgement unit 17, each of the image data pieces being $X_0$ distant from the edge of each die. The defect judgement unit 17 judges defect from the image data 53A, the image data 53B, and the image data 53B to decide which image data a defect exists in and sends image data containing the defect to the overall control unit 18. Next, a similar comparison inspection is executed in respect of areas adjoining the areas 52A, 52B and 52C, respectively. In this manner, with respect to one stripe area of 3 dies, the comparison inspection is executed and the inspection conditions are decided as to whether or not they are proper.

By using FIG. 2, processing of image data will be described. The defect judgement unit 17 operates in accordance with the following procedures. Namely, a digital signal 14 of the stripe area 51 irradiated with electrons is stored in the image memory 30. Data of the stored digital signal 14 is divided into a plurality of channels each having 128 pixels. The image distributor 31 performs judging a defect through the cell comparison process which utilizing the repetiveness of memory cells in memory mat 42 and in which each image data having coordinates within a die in the channel which range 128 lines from the constant value ($X_0$) is distributed to the same PE 32 and through the die comparison process as well, and makes a decision that coordinates decided as being defective through either process is a defect.

When a recipe is prepared through the trial inspection shown in FIG. 4 (*a*), an actual inspection is executed as shown in FIG. 4 (*b*). The operator selects a recipe suitable for a semiconductor wafer 6 representing an inspection objective with the help of the console 19. The overall control unit 18 reads the selected recipe (step 411), loads the semiconductor wafer 6 (step 412) and mounts it on the sample holder 9. Optical conditions are set (step 413) and alignment of the semiconductor wafer 6 is conducted (step 414). Principal optical system conditions are an extraction voltage of the electron source 1, a deflection current of deflector 3, an excitation voltage of objective lens 4, a voltage applied to the charge-up control electrode 5 and a voltage applied to the reflection plate 11. Next, an image of the standard sample piece 21 is acquired and the conditions are corrected for a proper image. After the alignment, an image for calibration is acquired and an image acquisition condition such as gain of the detector 13 is set such that a proper light quantity free from generation of light quantity shortage and light quantity surplus can be obtained (step 415). Thereafter, an image is detected in respect of a preset inspection region to judge a defect (step 416). For focus correction, the excitation current value of objective lens 4 is controlled on the basis of the height of semiconductor wafer 6 detected by the Z sensor 8. An analog signal representing a signal detected by the detector 13 is converted into a digital signal 14 by means of the AD converter 15. On the basis of the acquired image, a defect is determined through procedures similar to those during recipe preparation. The results including defect information 16 of defect judgement result and inspection conditions are stored (step 417) and the semiconductor wafer 6 is unloaded (step 418), thus ending the inspection.

Figure 6:
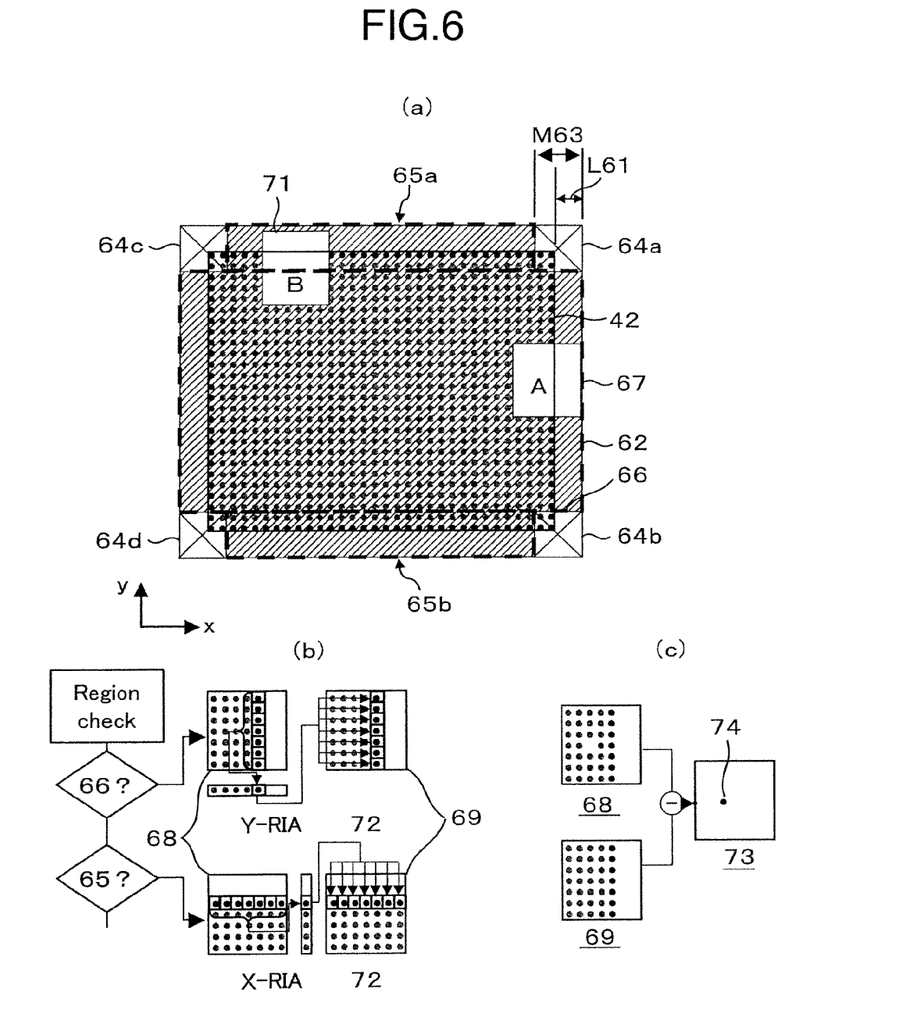
FIG. 6 is a plan view of a memory mat showing the contents of a cell comparison inspection.

The memory mat is illustrated in FIG. 6 in plan view form to show the contents of the cell comparison inspection. In the cell comparison inspection, judgementing a defect is carried out on the basis of the FR-MA method. In FIG. 6 (*a*), a rectangular area defining the memory mat 42 is expanded by an L dimension 61 to consider a region 62 and besides a region is considered which is obtained by reducing the region 62 by an M dimension 63. The L dimension 61 indicates an upper-limit of possible shift of the set region and the M dimension 63 is twice the L dimension 61. The region 62 can be divided into 3 areas. More particularly, there are corner areas 64a, 64b, 64c, and 64d which are each internal of each corner of the region 62 by M dimension 63, upper/lower end areas 65a, 65b, 65c, and 65b which are internal of the upper/lower sides by M dimension and the other area 66. The corner area 64 cannot be expected for the repetiveness because when considering a shift of the region, there is a possibility that the corner inside the memory mat will move to an arbitrary location within the region, the upper/lower end area 65 is an area expected for repetiveness in at least X direction and the other area 66 is an area expected for repetiveness in Y direction.

In case the inspection image 68 of 128 pixels×128 lines distributed to the PE 32 corresponds to an area A 67, all pixels of the distributed image have repetiveness in Y direction. Then, Y-RIA 70 is carried out in which images at intervals of a repeative pitch in Y direction are added and averaged to once prepare an image and by rearranging the added and averaged image, an added and averaged image 69 is generated. Likewise, in case the inspection image 68 of 128 pixels×128 lines distributed to the PE corresponds to an area B 72, all pixels of the distributed image have repetiveness in X direction. Then, X-RIA 72 is carried out in which images at intervals of a repeative pitch in X direction are added and averaged to once prepare an image and by rearranging the added and averaged image, an added and averaged image 69 is generated. As a difference between the detected image 68 and the added/averaged image 69, a difference image 73 is operated. An area in which the difference value of difference image 73 is larger than the set defect judgement threshold value is determined as a defect 74.

Figure 7:
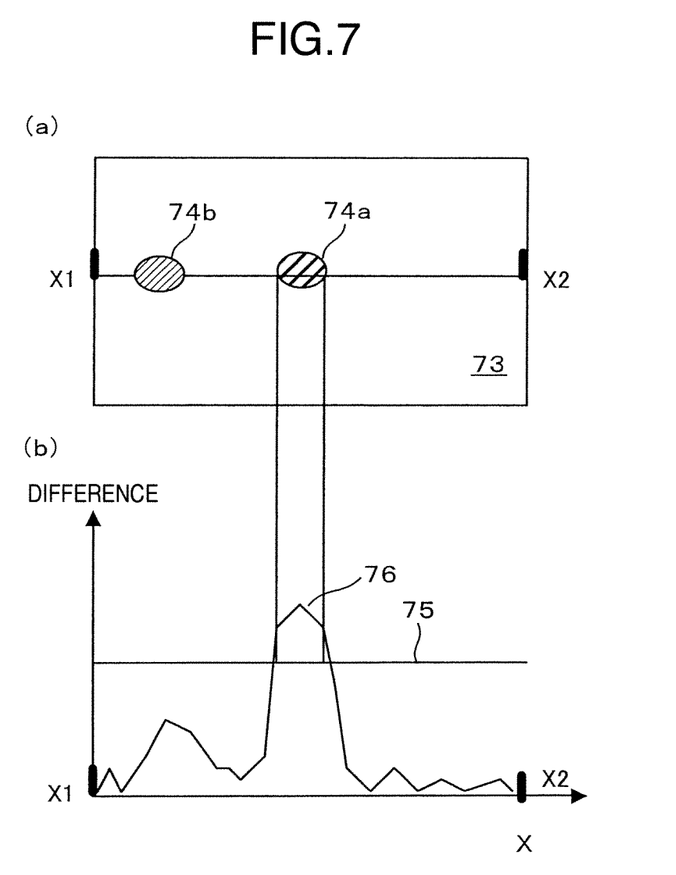
FIG. 7 is a diagram of a screen showing an example of an image.

The operation of difference will now be described supplementarily with reference to FIG. 7. An example of the image is illustrated in FIG. 7 showing an image in FIG. 7 (a) and a graph in FIG. 7 (b) illustrating differences as a result of comparison of gradation values of individual pixels on a line segment between $X_1$ and $X_2$ at (a) in FIG. 7 with that of a reference image. As shown in FIG. 7 (a), in general, the difference image 73 contains an actual defect area 74a and an area 74b which is not a defect but has a large difference. For the causes of the region 74b are unevenness due to noise components of the image and these are increased when charge-up occurs on the semiconductor wafer. For discriminating the defect and the other region, a threshold value 75 for the difference is provided and so, an area having a difference larger than the threshold value is determined as a defect. The difference value 76 and a coordinates of the corresponding defect 74a constitute defect information on distributed partial images 33 shown in FIG. 2. In this manner, it is possible for the area other than the corner area 64 shown in FIG. 6 (a) to be determined as a defect.

Figure 8:
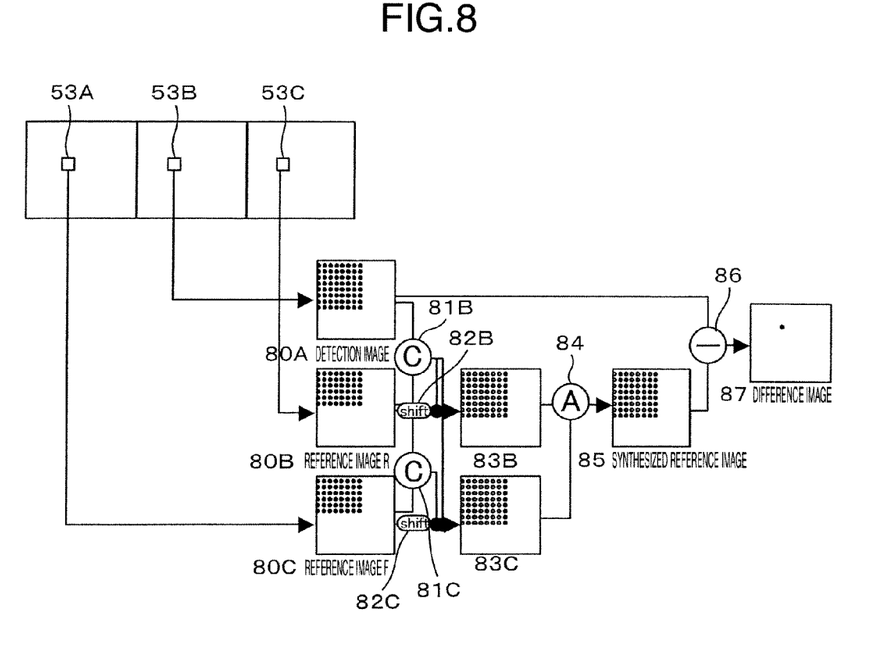
FIG. 8 is a diagram showing diagrammatically the contents of image processing.

Next, the die comparison inspection will be explained by using FIG. 8. The contents of image processing is illustrated diagrammatically in FIG. 8. Partial image data 53A, 53B, and 53C are distributed to the same PE 32 shown in FIG. 2. Assumptively, the partial image data 53A, 53B, and 53C correspond to mutually adjoining dies. The partial image data 53A, 53B, or 53C is of 128 pixels×128 lines. The die comparison aims at deciding whether the image data 53B of the central die is defective and so, to avoid confusion, the image name will be redefined in the die comparison. The image data 53B, image data 53A, and image data 53C will be called a detected image 80A, a reference image F 80C and a reference image R 80B, respectively.

In accordance with captured range of image, or while cutting out image, coordinates among image data will often shift by mechanical errors and so on. Accordingly, there is a possibility that locations of patterns of the reference image F 80C and reference image R 80B will displace from that of the detected image 80A and they cannot be compared with each other as they are. Then, shifting amount calculation units 81B and 81C each calculates a shifting amount by mutual correlation or a shifting amount by a sum of absolute difference, and image shifting units 82B and 82C shifts the reference image R 80B and reference image F 80C, respectively, thus preparing position matched reference images 83B and 83C. Since the position matched reference images 83B and 83C have each a pattern at the same position as the detected image 80A, an image synthesizer 84 adds and averages these images, thereby providing a composed reference image 85 of less noise. Next, a difference image operation unit 86 operates a difference between the detected image 80A and the composed reference image 85 to provide a difference image 87.

Figure 9:
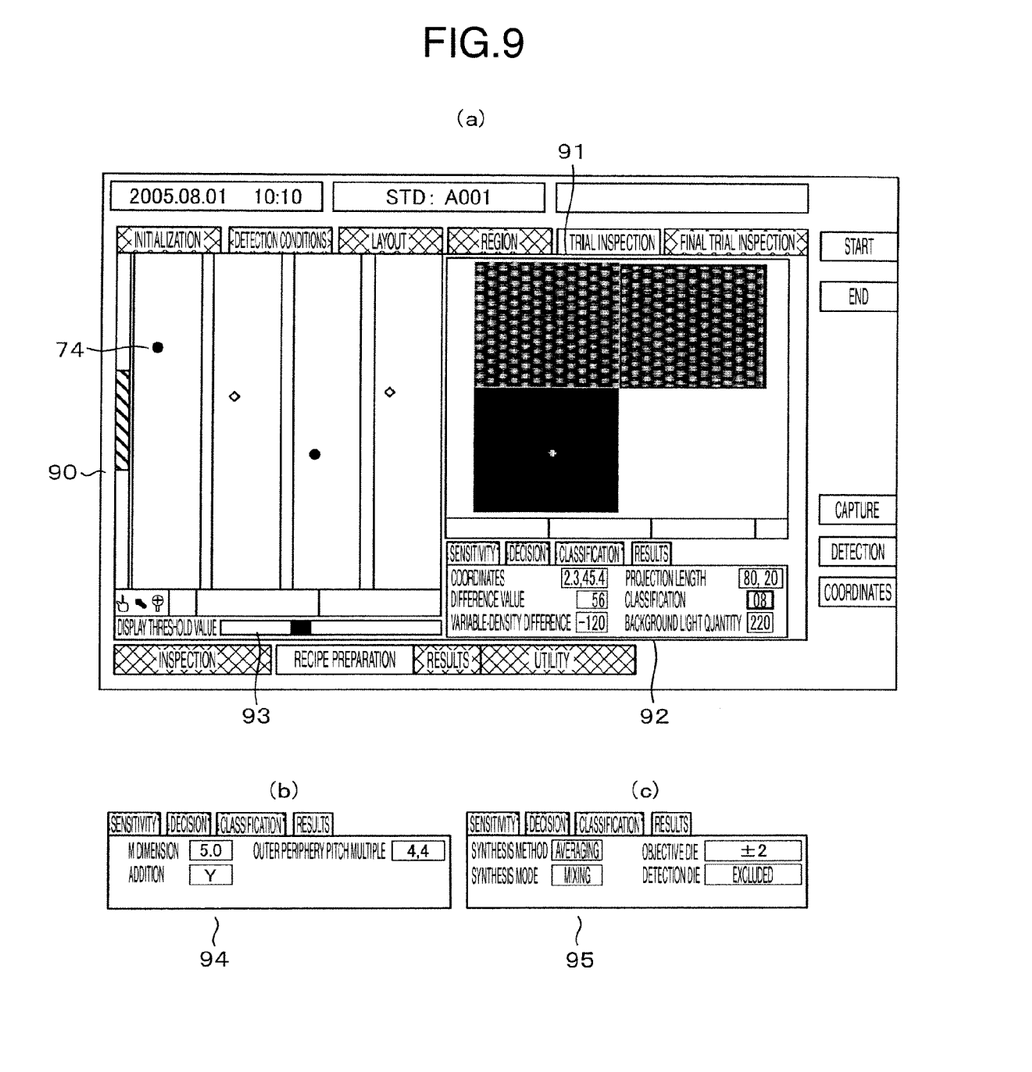
FIG. 9 is a diagram of a screen displayed on a display of console.

FIG. 9 illustrates a picture displayed on the display of console 19, showing an example of display of defect information. The inspection apparatus determines that a region of pixels having difference values in excess of the threshold value is a defect and therefore, even when the large difference value will not always correspond to a true defect. Then, an image of the defect is displayed on an image display area 91 to provide the inspection apparatus with the function to enable the operator to decide whether a defect is present or not. Further, by making the threshold value 75 shown in FIG. 7 (b) a display threshold value which is not fixed but variable, behavior of the detection of the defect can be confirmed from the image.

On the left side of the screen, a stripe map 90 for diagrammatically indicating a defect 74 on a stripe area in the form of a mark is arranged and on the right side, the image display area 91 for displaying an actual image of a defect is arranged. The stripe map 90 and image display area 91 are displayed in parallel on the single screen but they may be displayed on separate displays. Further displayed on the screen are a defect information display area 92 and a display threshold value adjusting tool bar 93. In the defect information display area 92, information such as a defect coordinates, a projection length, a difference value, a variable-density difference and a background brightness in the defect information, a classification code the operator inputs and so on are displayed. The display threshold value adjusting tool bar 93 is used for adjusting the display threshold value.

By designating the defect 74 displayed on the stripe map 90 with the help of an input means such as a mouse pointer, the operator makes image information of the defect 74 be displayed on the image display area 91 and coordinates information and the like to be displayed on the defect information display area 92. To ensure that a higher definition image of the defect 74 can be regained and image data stored in the image memory 30 can be displayed on the image display area 91, designation buttons may be added for the screen.

The classification code is provided for the defect information display area 92 to permit the operator to sort the defect by watching the defect image. Classification is categorized as foreign particle, scratch, pattern-cut and short-circuiting and the operator writes the classification information to a classification box. The defect 74 displayed on the stripe map 90 can be classified and displayed in different colors. When the classification is changed, the display format of defect 74 on the stripe map 90 changes.

The higher the aforementioned display threshold value, the more the number of defects 74 to be displayed on the stripe map 90 decreases, facilitating analysis such as sorting of defects but there is a possibility that the number of even true defects not to be determined as defects will increase. On the other hand, the lower the display threshold value, the more the number of defects 74 increases and the defects are less overlooked but there is a possibility that the number of nuisance will increase. Only the defects having difference values in excess of the display threshold value are displayed on the stripe map 90 and therefore, by changing the display threshold value by means of the display threshold adjusting value tool bar 93, a proper display threshold value can be set while watching comparatively with the defect image.

In the defect information display area 92, a memory repeat-ive region image composition condition setting dialogue 94 as shown in FIG. 9 (b) and an all-region-image composition condition setting dialogue 95 can be displayed and with the help of these dialogues, an image composition condition can be set.

Through these working processes, the inspection conditions are confirmed and if satisfactory, the confirmation work ends, otherwise inspection conditions are set again and a trial inspection is conducted. In case of satisfaction, the recipe is conserved and the semiconductor wafer is unloaded.

Figure 10:
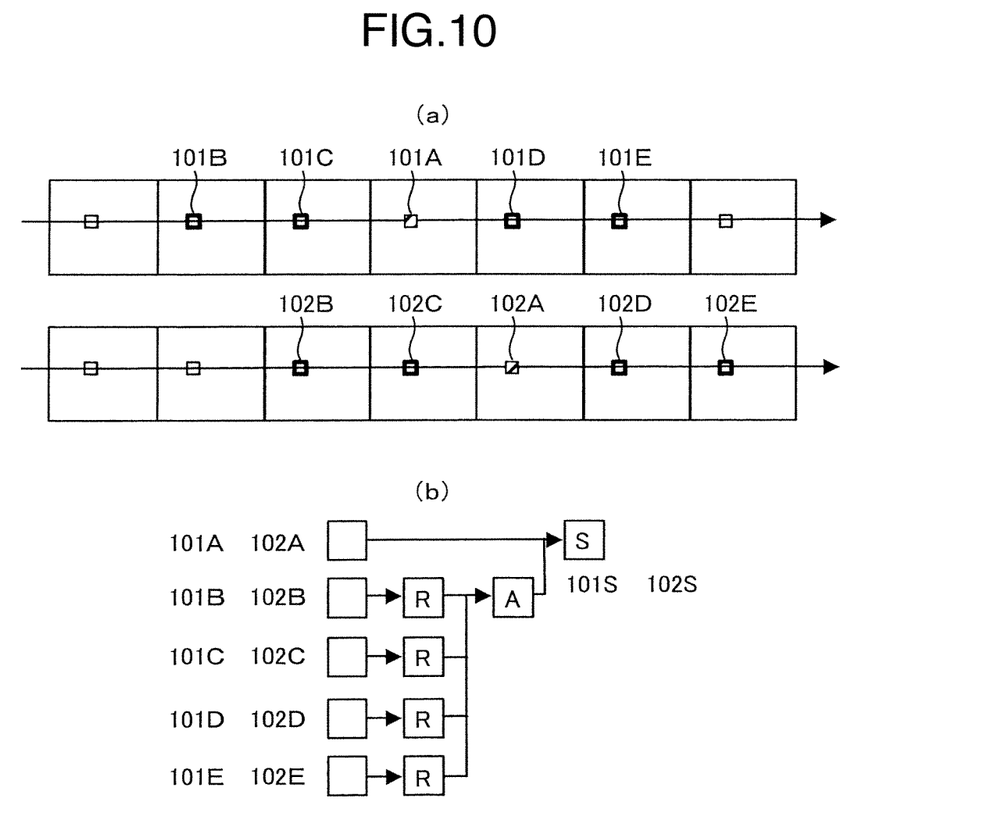
FIG. 10 is a diagram showing diagrammatically the contents of image processing.

The contents of image processing is illustrated diagrammatically in FIG. 10. In the extraction of a defect in the image data as shown in FIG. 8, in addition to the die of an inspection objective, preceding and succeeding dies are used as reference images and 3 pieces of image data are used. In the present embodiment, an example will be described in which 5 pieces of image data are used. The larger the number of pieces of image data, the more noises in the image can be decreased.

By using pieces of image data of 4 dies including an image 101A of a detection die and preceding and succeeding images 101B to 101E of 4 dies, reference images are operated and a difference image 101S is operated. After completion of processing the image 101A of detection die, pieces of image data of images 102B to 102E of 4 dies preceding and succeeding an image 102A of the detection die are used to operate reference images and operate a difference image 102S. This is carried out in succession in respect of images of detection dies.

How to use the individual images is illustrated in FIG. 10 (b) and marks R, A, and S designate a displacement correction image, a composed reference image, and a difference image resulting from an operation of comparing an image of a detection die with a reference image, respectively. Firstly, correction of mutual displacement is carried out for the four images 101B to 101E. Next, these four images are added and averaged to generate composed reference images which in turn are compared with the image 101A of detection die, obtaining a difference image 101S. A similar process is applied also to the detected image 102A to obtain a difference image 102S.

Figure 11:
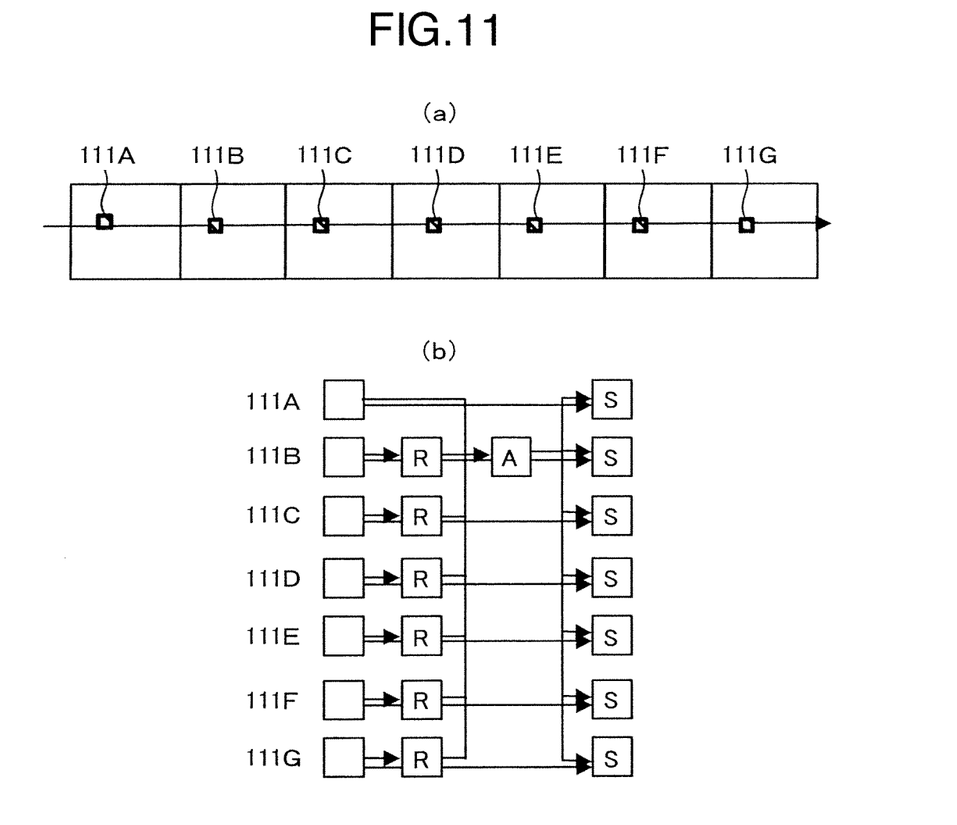
FIG. 11 is a diagram showing diagrammatically the contents of image processing.

Like FIG. 10, FIG. 11 diagrammatically illustrates the contents of image processing. In the example of FIG. 10, the composed reference images are generated without using the image 101A of detection die, the composed reference images are compared with the image 101A of detection die to obtain a single difference image 101S and then, in order to generate the difference image 102S concerning the image 102A of the next detection die adjoining the image 101A of detection die, the images 101C and 101A are re-used as being the images 102B and 102C, respectively, and the image 101E is reused as the image 102D, thus generating the single difference image 102S. Accordingly, for a single detection die image, a single difference image is generated through a single operation. Contrary thereto, in the present embodiment, for a plurality of images, a plurality of difference images can be generated through a single operation and to great advantage, time necessary for operation can be shortened.

As shown in FIG. 11 (a), an example will be considered where all images 111A to 111G of, for example, 7 dies are compared mutually to generate difference images. As shown in FIG. 11 (b), correction is made for displacement from the image 111A to generate images of mark R which in turn are added and averaged to acquire a composed reference image of mark A. Subsequently, the difference between the composed image of mark A and each of the 7 images 111A to 111G is operated, acquiring 7 difference images S.

Figure 12:
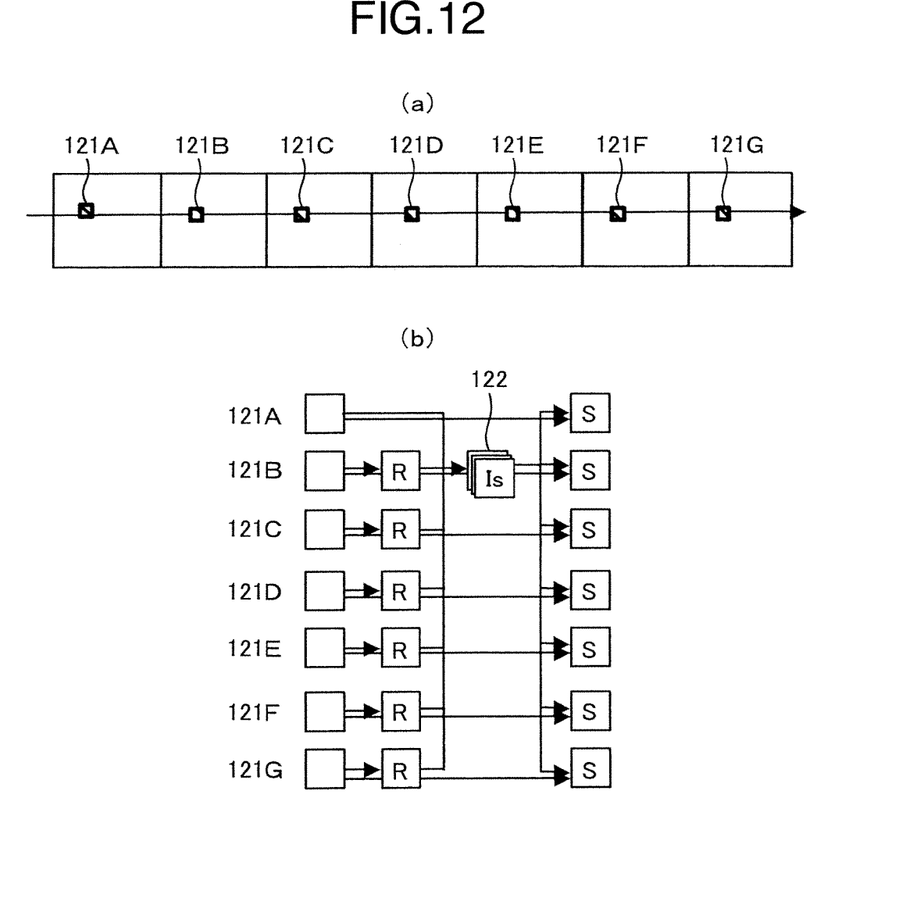
FIG. 12 is a diagram showing diagrammatically the contents of image processing.

Like FIG. 10, FIG. 12 diagrammatically illustrates the contents of image processing. As shown in FIG. 12 (a), for 7 images 121A to 121G, correction is made for displacement amount from the image 121A as shown in FIG. 12 (b). Next, in contrast to the simple addition and average of the 7 images as in FIG. 11, a sequence image Is 122 resulting from integration of the images before addition is prepared and each of the images 121A to 121G are compared with the sequence image Is 122 to operate differences. Because the image is not a simple average image, a median, an average excluding outliers, an average of maximum and minimum and the like can be used in place of the average value. Further, by operating the average and dispersion, an operation is possible in which a difference triple or more larger than dispersion can be determined as a defect. While an explanation has been given of determination by the image sequence, these values can be operated structurally in addition to the composed reference image. This modification is advantageous in that high-sensitivity defect decision can be achieved through highly functional operation.

Figure 13:
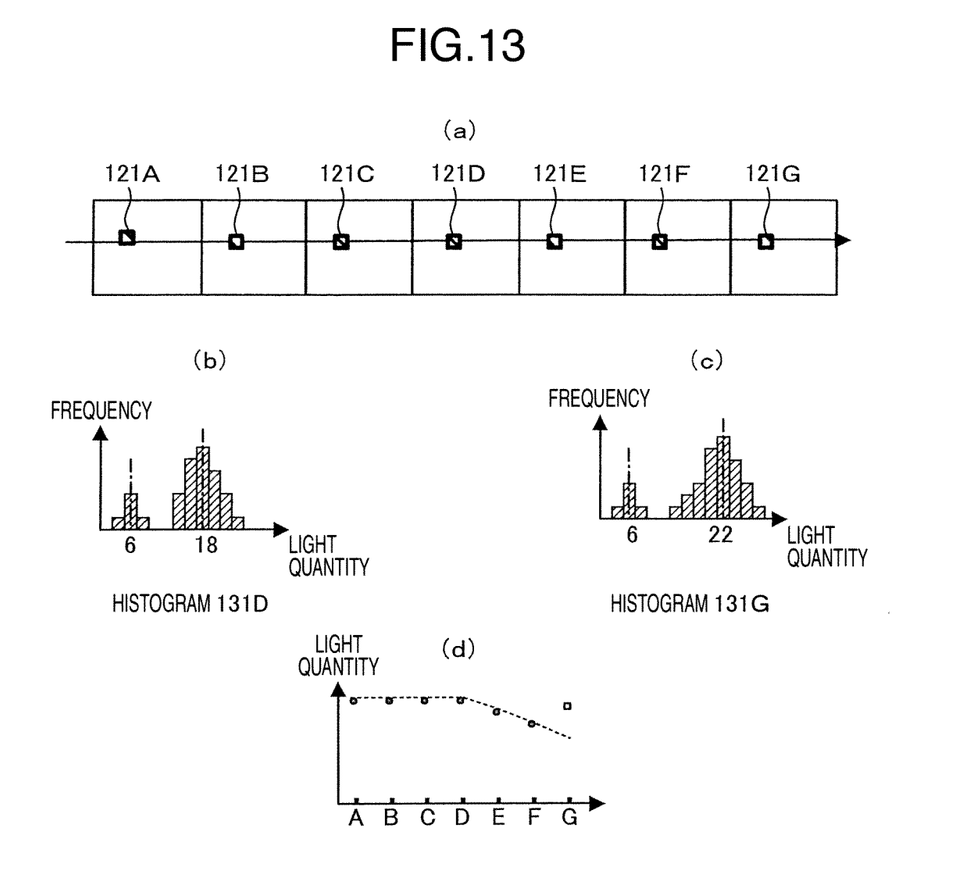
FIG. 13 is a diagram showing diagrammatically the contents of image processing.

Like FIG. 10, FIG. 13 diagrammatically illustrates the contents of image processing. The central portion of the semiconductor wafer sometimes differs in gradation value of image data from its end. For example, as shown in FIG. 13 (a), an image is acquired in such a manner that a die containing a left end image 121A of, for example, 7 dies includes the central portion of a semiconductor wafer and a die containing a right end image 121G includes the end of the semiconductor wafer, and comparison inspection is carried out in respect of images 121A, 121B, 121C, 121D, 121E, 121F and 121G. Since the region of insulation film of die differs in thickness between the central portion of semiconductor wafer and the end of thereof, a distribution of gradation values is not uniform for the individual images. For example, a histogram of image gradation values of the image 121D becomes a histogram 131D shown in FIG. 13 (b) and a histogram of image gradation values of the image 121G becomes a histogram 131G shown in FIG. 13 (c).

When the gradation values differ, the mutual difference among images is large even after the average value is acquired and the defect cannot be detected. As a countermeasure against it, a band-pass filter is applied to the input to thereby extract only a desired frequency component to thereby eliminate the influence of gradation value change. Or, a correction process is conducted to make average gradation values of a square of about 20 pixels coincident with each other. Alternatively, when a histogram of the image 121G at the end of semiconductor wafer differs from the other as shown in FIG. 13 (d), the image 121G is excluded and the gradation value of a detected image is presumed through interpolation or extrapolation of the remaining images.

As has been described, according to the reference image composition by using combination of FR-RIA and die unit composition, a circuit pattern inspection apparatus and a circuit pattern inspection method are provided which can judge defect with height sensitivity not only in the memory mat, but also overall die surface including the interior of memory mat, the outer-most periphery of memory mat and the peripheral circuit. In the foregoing embodiments, the inspection apparatus for circuit pattern has been described as generating an image by irradiating an electron beam on a sample but even in an inspection apparatus for circuit pattern adapted to generate an image by illuminating light on a sample, the invention described in the embodiments can be carried out.

REFERENCE SIGNS LIST

1 Electron source
2 Electrons
3 Deflector
4 Objective lens
5 Charge-up control electrode
6 Semiconductor wafer
7 XY stage
8 Z sensor
9 Sample base
10 Secondary signal
11 Reflection plate
12 Convergence optical system
13 Detector
14 Digital signal
15 AD converter
16 Defect information
17 Defect judgement unit 18 Overall control unit
19 Console
20 Optical microscope
21 Standard sample piece
30 Image memory
31 Image distributor
32 PE
33 Defect information on partial images
34 Information unifier
40 Die
41 Memory mat group
42 Memory mat
43 Memory cell
51 Stripe area
54 Trial inspection coordinate
55 Memory region
90 Stripe map
91 Image display area
92 Defect information display area
93 Display threshold value adjusting tool bar
94 Repeative pattern composition condition setting dialogue
95 All-region-image composition condition setting dialogue
101, 102 Image

The invention claimed is:

1. A circuit pattern inspection apparatus, comprising:
an image detection unit configured to acquire an image of a circuit pattern composed of multiple die having a repetitive pattern; and
a defect judgment unit configured to:
compose, in respect of a divided detected image of the acquired image, reference images by switching addition objects depending on regions of the repetitive pattern and other regions, and
compare at least one of the composed reference images with the detected image to detect a defect,
wherein the defect judgment unit is configured to, when a region of the repetitive pattern is included in divided detected images of the acquired image, compose the reference images by adding a portion of the repetitive pattern thereto in a repetition direction that is determined by a position of a region corresponding to the divided detected images.

2. A circuit pattern inspection apparatus according to claim 1 further comprising:
a display unit configured to display an image of said detected defect.

3. A circuit pattern inspection apparatus according to claim 1, wherein said composed reference images are generated by a process for operating arbitrary statistic such as addition, average, an average value excluding outliers or an average value of maximum and minimum of said plural detected images.

4. A circuit pattern inspection apparatus according to claim 1, wherein the region of the repetitive pattern and the other regions are determined based on whether the divided detected images include regions defined by a predetermined dimension at the outer periphery of a region set as the repetitive pattern.

5. A circuit pattern inspection apparatus according to claim 4, wherein the repetition direction is judged in accordance with a positional relation between the regions defined by the predetermined dimension and regions corresponding to the divided detected images.

6. A circuit pattern inspection apparatus according to claim 1, wherein the defect judgment unit, when the region of the repetitive pattern is included in the divided detected images, the reference images are synthesized by way of rendering images at an interval of a repetitive pitch in the repetitive direction added and averaged and by rearranging the added and averaged images.

7. A circuit pattern inspection apparatus according to claim 1, wherein the repetitive pattern is a memory mat.

8. A circuit pattern inspection method, comprising:
acquiring an image of a circuit pattern composed of multiple die having a repetitive pattern,
synthesizing, in respect of a divided detected image of the acquired image, reference images by switching addition objects depending on regions of the repetitive pattern and other regions, and
comparing at least one of the reference images with the detected image to detect a defect,
wherein, when a region of the repetitive pattern is included in divided detected images of the acquired image, the reference images are synthesized by adding a portion of the repetitive pattern in a repetition direction that is determined by a position of a region corresponding to the divided detected images.

9. A circuit pattern inspection method according to claim 8, wherein said composed reference images are generated through a process for operating arbitrary statistical operation such as addition, average, an average value excluding outliers or an average value of maximum and minimum of said plural detected images.

10. A circuit pattern inspection apparatus according to claim 8, wherein the region of the repetitive pattern and the other regions are determined based on whether the divided images include a region defined by a predetermined dimension at the outer periphery of regions set as the repetitive pattern.

11. A circuit pattern inspection apparatus according to claim 10, wherein the repetition direction is judged in accordance with a positional relation between the region defined by the predetermined dimension and regions corresponding to the divided detected images.

12. A circuit pattern inspection method according to claim 8, wherein when the region of the repetitive patterns is included in the divided detected images, the reference images are synthesized by way of rendering images at intervals of a repetitive pitch in the repetition direction added and averaged and by rearranging the added and averaged images.

13. A circuit pattern inspection method according to claim 8, wherein the repetitive pattern is a memory mat.

* * * * *